United States Patent [19]

Muz

[11] Patent Number: 4,907,594
[45] Date of Patent: Mar. 13, 1990

[54] METHOD FOR THE DETERMINATION OF THE SATURATION OF THE BLOOD OF A LIVING ORGANISM WITH OXYGEN AND ELECTRONIC CIRCUIT FOR PERFORMING THIS METHOD

[75] Inventor: Edwin Muz, Reutlingen, Fed. Rep. of Germany

[73] Assignee: Nicolay GmBH, Kirchheim, Fed. Rep. of Germany

[21] Appl. No.: 210,089

[22] Filed: Jun. 22, 1988

[30] Foreign Application Priority Data

Jul. 18, 1987 [DE] Fed. Rep. of Germany ....... 3723881

[51] Int. Cl.$^4$ ................................................ A61B 5/00
[52] U.S. Cl. ..................................... 128/633; 128/664; 128/665
[58] Field of Search ................ 128/664, 667, 633–634, 128/690, 691

[56] References Cited

U.S. PATENT DOCUMENTS 3,412,729  11/1968  Smith .................................. 128/667
4,700,708  10/1987  New et al. ........................... 128/633

FOREIGN PATENT DOCUMENTS 0019478  11/1980  European Pat. Off. ............. 128/633
3222279  12/1983  Fed. Rep. of Germany ...... 128/666

OTHER PUBLICATIONS

Geddes, Leslie Alexander, "Principles of Applied Biomedical Instrumentation", Chapter 5–Photoelectric Transducers, pp. 95–101, published by John Wiley & Sons, Inc.

Primary Examiner—Kyle L. Howell
Attorney, Agent, or Firm—Joseph Scafetta, Jr.

[57] ABSTRACT

A method is disclosed for the determination of the saturation of the blood of a living organism with oxygen and an electronic circuit for performing this method is also disclosed.

The method resides in red light and infrared radiation being simultaneously beamed into living tissue and the mixed residual radiation emanating from the irradiated tissue being received by a phototransistor 18 and the infrared radiation contained in the mixed residual radiation being received by an identical phototransistor 17 with a green filter 20 arranged in front of it. The measured intensity of the residual infrared radiation is subtracted from the measured intensity of the mixed residual radiation by an electronic circuit so as to obtain the intensity of the residual red light radiation and the residual infrared radiation. The saturation of the blood with oxygen can be computed from the values represented by these intensities of the residual infrared and red light radiations.

The electronic circuit includes two light-emitting diodes 15 and 16 for infrared radiation and for red light, respectively, and two identical phototransistors 17 and 18. A green filter 20 is arranged in front of the phototransistor 17. Via a comparator, photocurrents are generated in the phototransistors 17 and 18 which have DC components of equal value for the infrared radiation, on the one hand, and for the red light, on the other hand. The photocurrents generated by the mixed residual radiation in the photo transistor 18 and by the infrared radiation in the photo transistor 17 are modulated by the heartbeat. The electric signal derived from the modulation of the photocurrent of the phototransistor 17 is subtracted in a subtracting circuit 41 from the electric signal derived from the modulation of the photocurrent of the phototransistor 18.

7 Claims, 2 Drawing Sheets

METHOD FOR THE DETERMINATION OF THE SATURATION OF THE BLOOD OF A LIVING ORGANISM WITH OXYGEN AND ELECTRONIC CIRCUIT FOR PERFORMING THIS METHOD

CROSS-REFERENCE TO RELATED APPLICATION

This application is related to U.S. patent application Ser. No. 210,040, filed June 22, 1988, in the name of the same inventor by the same assignee.

BACKGROUND OF THE INVENTION

1. Field of the Invention

The invention relates to a method for the determination of the saturation of the blood of a living organism with oxygen, in which radiation in a first and in a second wavelength range, in which the absorption coefficients of oxyhaemoglobin ($HBO_2$), on the one hand, and reduced haemoglobin (Hb), on the other hand, show different ratios, is simultaneously beamed into living tissue, and the mixed residual radiation emanating from the irradiated tissue is received and measured in two different wavelength measuring ranges by two optoelectronic receiver elements, and, on the basis of these measurements, the intensities of the residual light in the two wavelength ranges are determined.

2. Description of the Related Art

Methods of this kind are known. Determination of the oxygen saturation by known methods is, for example, described in detail in the chapter "NON-INVASIVE SPECTROPHOTOMETRIC ESTIMATION OF ARTERIAL OXYGEN SATURATION" of the book "Non-Invasive Measurements" by I. Yoshiya and Y. Shimada, published by Academic Press Inc. in 1983.

To determine the oxygen saturation, precise values for the residual radiation of two different wavelengths are, however, required. If radiation of two different wavelength ranges is beamed simultaneously into the tissue, the two components get mixed. Consequently, when the residual radiation is then received in the optoelectronic receiver elements, one wavelength range has to be filtered out in each optoelectronic receiver element. However, as mentioned above, the two wavelength ranges for the determination of the oxygen saturation cannot be selected arbitrarily. It is, therefore, not possible to assume that wavelength ranges will be selected for which suitable filters are available at reasonable cost. The conditions involved are particularly difficult to meet if for physical reasons the optoelectronic elements and filters have to be as small as possible as is the case, for example, for measurements at an earlobe, a finger or a toe.

It is also known that the radiation of the two wavelength ranges employed can be separated by pulsed alternate beaming of the radiation of the two wavelength ranges so at any instant in time radiation of one wavelength range only will be beamed through the tissue. Difficulties in circuit technology do, however, result in this case since the pulse frequency of the blood also has to be taken into account and to some extent the results have to be stored.

SUMMARY OF THE INVENTION

The object of the invention is to so improve the method mentioned initially that it can be performed with a substantially less degree of effort.

This object is accomplished in the method mentioned initially by the intensity of the residual radiation within the first wavelength range being measured by the one optoelectronic receiver element and by the common intensity of the residual radiation within a larger measuring range encompassing both wavelength ranges being measured by the second optoelectronic receiver element, and by the measured intensity of the residual radiation of the one wavelength range being subtracted from the measured intensity of the larger measuring range by means of an electronic circuit in order to determine the intensity of the residual radiation of the other wavelength range. Therefore, in the measuring procedure, a filter will be required for only one of the receiver elements. This enables selection of the two wavelength ranges in such a way as to permit use of available, simple and moderately priced filters which can be manufactured in miniaturized versions.

In an embodiment of the inventive method, infrared radiation can be used as the first wavelength range encompassed by one measuring range, and red light can be used as the second wavelength range since a green filter made of polymethyl methacrylate ester (PMMA) which is economically priced and can be manufactured in practically any size is commercially available for red light. The infrared radiation which is particularly well suited for this purpose, but can be filtered out with considerable effort only, can, therefore, be selected as the first wavelength range.

The invention also relates to an electronic circuit for performing the method which is characterized by two optoelectronic transmitting elements being provided, each of which is powered via an electronic control element, and one of which is intended for the emission of radiation within the first and the other for the emission of radiation within the second wavelength range, further by two identical optoelectronic receiver elements being provided, one of which is powered via one of three identical resistors and the other via the other two resistors connected in series, in order to measure the intensity of the residual radiation, further by a filter which blocks the radiation of the second wavelength range being arranged in front of the receiver element powered via the two resistors, further by the receiver elements together with their feeder resistors being connected to the input terminals of a comparator by means of connecting lines via RC circuits for filtering out the pulse rate present in the blood to be examined, with the control element in the supply line of the transmitting element for the first wavelength range being controlled via the RC circuit of the receiver element with a filter arranged in front of it and, consequently, directly by the photocurrent caused by the radiation of the first wavelength range, and with the other control element in the supply line of the transmitting element for the second wavelength range being controlled by the comparator, in order to obtain a DC component of the photocurrent for the receiver element receiving the radiation of both wavelength ranges which DC component is twice as large as that for the element receiving only the radiation of the first wavelength range, further by the connection line between the two resistors connected in series which carries the photocurrent resulting from the radiation of the first wavelength range being connected to one of the input terminals of an electronic subtraction circuit via a capacitor, and the connection line between the resistor and the receiver element for the photocurrent of both wavelength ranges being connected to the other input terminal of the electronic subtraction circuit via a second capacitor.

When passing through living tissue, radiation is mainly absorbed by tissue, bones and the like and also by the venous blood which is unimportant with respect to the determination of the oxygen saturation. This results in an essentially constant absorption of the light during measurement. The absorption of light by the arterial blood does, however, fluctuate with the pulse or heart rate. It is, therefore, known to measure only the modulated component of the photocurrents obtained in the process of measuring. However, the amplitude of the modulation increases proportionally to the DC component of the photocurrent. To obtain a precise measurement, it is, therefore, important to keep the DC component of the two wavelength ranges at identical levels and, consequently, to maintain the DC component of the photocurrent of the receiver element excited by both wavelength ranges twice as large as the DC component of the photocurrent of the other receiver element excited by a single wavelength range only. This maintenance is achieved in a simple way, in accordance with the invention, by the comparator featured in the circuit according to the invention. Use of three identical resistors in the feeder lines of the receiver elements enables tapping of the modulation voltages of the photocurrents of the two receiver elements at two identical resistors.

Since the inventive method employing the circuit according to the invention allows the use of a reasonably priced filter available in practically all sizes at one receiver element only, the carrier of the device according to the invention can be implemented with very small dimensions, which enables it to be brought into close contact with small parts of the body such as, for example, an earlobe, finger, toe or the like. In a particularly advantageous embodiment of a device for performing the method according to the invention, the carrier for holding the optoelectronic components close to a finger or a toe can, therefore, be designed as a cap which can be placed over the outer end of a finger or a toe and which contains a soft, elastic inner wall which together with the cap encloses a pressure chamber that can be connected to a source of compressed air.

BRIEF DESCRIPTION OF THE DRAWINGS

The invention is explained in detail in the following description of embodiments illustrated in the drawings in which.

DETAILED DESCRIPTION OF THE PREFERRED EMBODIMENTS

Figure 1:
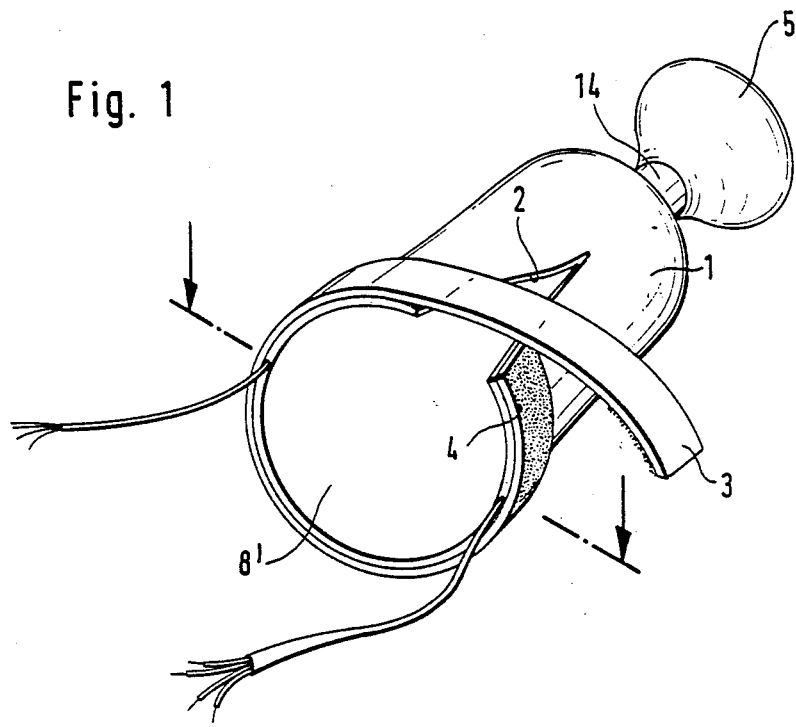
FIG. 1 is a perspective view of the embodiment of a cap with a ball as the source of compressed air.
Figure 2:
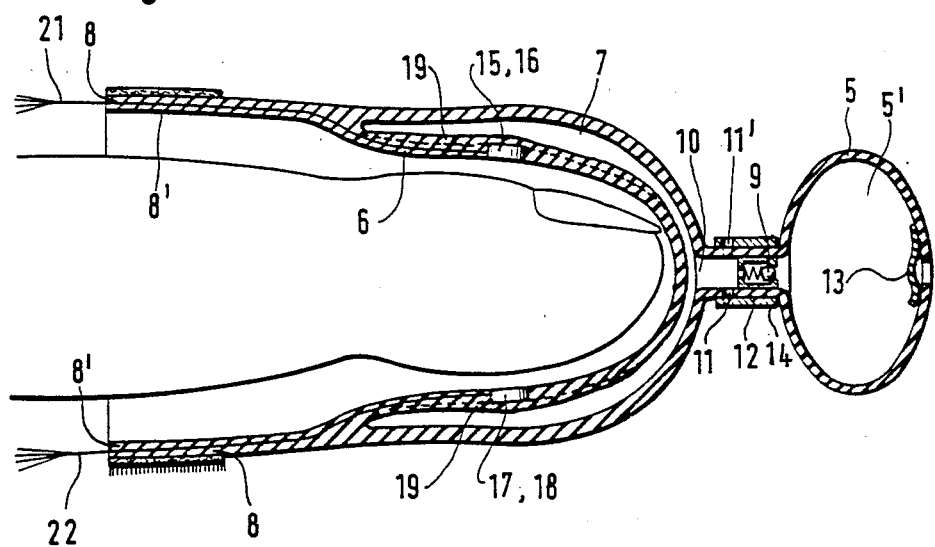
FIG. 2 is an axial cross-section of the embodiment as shown in FIG. 1.

The embodiment depicted in FIGS. 1 and 2 comprises a cap 1 which can be placed on the two distal joints of a finger or a toe. The cap 1 has a slit 2 extending from its open end and carries at the edge 8 of its opening a textile clinging closure, one part 3 of which has a large number of protruding, hook- or mushroom-shaped stubbles and the other part 4 of which has a large number of loops so parts 3 and 4 will cling together when pressed against each other.

At its closed end, cap 1 has an opening 10 which communicates with the cavity 5' of a ball 5 which is connected to cap 1.

In order to form a double-walled structure, a soft, elastic inner wall 6 having the shape of a cap is attached with the edge 8' of its opening at some distance from the inner open edge of cap 1 and encloses together with cap 1 a pressure chamber 7 which is connected to the cavity 5' of the ball 5.

The cap 1 and the soft, elastic wall 6 consist of natural or silicon rubber. The cap 1 exceeds the inner wall 6 in thickness, however, and is, therefore, less expandable.

A one-way valve 9 is located in a connection 14 between cap 1 and ball 5. By compression of ball 5, air can be pressed through valve 9 into the pressure chamber 7, but cannot escape back through valve 9. A venting opening 11 is provided on the side of the connection 14 facing the pressure chamber 7 between ball 5 and cap 1 in order to vent the pressure chamber 7. The venting opening 11 can be opened or closed by a ring 12 which is similarly provided with a venting opening 11' and can be rotated on the connection 14. Ball 5 is, furthermore, provided with an aspiration valve 13 acting as a one-way valve.

The cap 1 may, in accordance with the angle between the two distal, outmost, relaxed joints of a finger or a toe be of slightly arched shape to facilitate rotating the cap 1 into the desired position with respect to the finger or the toe when placing the cap 1 on a finger or a toe.

Two light-emitting diodes 15 and 16 are arranged adjacent to each other approximately in the area of the proximal end of the nail bed at the inner wall 6 to serve as optoelectronic transmitting elements. Two identical silicon phototransistors 17 and 18 are arranged as optoelectronic receiver elements in diametrally opposed relation to the transmitting elements. Since the transmitting elements and also the receiver elements are arranged adjacent to each other, only one of these adjacent elements is shown, in each case, in FIG. 2. In the area of the optoelectronic elements, the thickness of the inner wall 6 is increased. This thicker wall area 19 extends from an edge of the inner wall connected to the cap 1 to an area shortly before the closed tip of the cap-shaped inner wall 6. Two stiff sections formed thereby ensure that the optoelectronic elements 15 through 18 will always touch the finger or toe in precisely defined locations without tilting. The two stiff sections may, however, also form a band (not shown) extending from edge to edge of the inner wall 6. Two wires are connected to each of the elements 15 through 18 and can be led out together in the case of adjacent elements to form one cable 21 and 22, in each case. It is, however, also possible, although it is not shown, particularly if the band-type thicker wall areas 19 are in the form of a single continuous thicker section extending over the closed tip of the inner wall 6, for the four wires of one pair of elements, for example, 15 and 16, to run in one cable 21 over the closed tip of the inner wall 6 to the other pair of elements 17, 18, from where all eight wires can be led out in a single cable 22.

Figure 3:
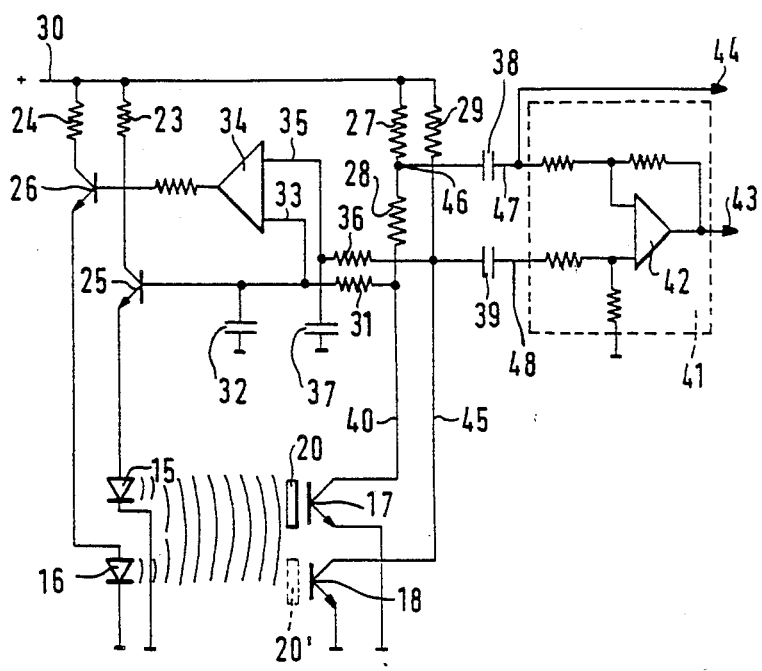
FIG. 3 shows a circuit for the embodiment as shown in FIGS. 1 and 2.

FIG. 3 shows a circuit which enables determination of the saturation of the blood of a living organism with oxygen using the cap 1 as described above. This determination is done by measuring the amounts of residual radiation emanating from the irradiated tissue by the two phototransistors 17 and 18.

As depicted in FIG. 3, the light-emitting diode 15 is powered via resistor 23 connected in series with control transistor 25 and the light-emitting diode 16 is powered via resistor 24 connected in series with control transistor 26. The light-emitting diode 15 emits infrared radiation in a first wavelength range of 800 to 940 nanometers and the light-emitting diode 16 emits red light in a wavelength range of around 660 nm.

Once the flows of radiation from the two light-emitting diodes 15 and 16 have penetrated the tissue, they mix to form a mixture of infrared and red radiation.

The collector of phototransistor 17 is connected to the positive terminal 30 of the power supply via two identical resistors 27 and 28 which are connected in series. This phototransistor 17 is covered by a filter 20 made of green polymethyl methacrylate ester (PMMA) which blocks the red component present in the mixture of radiation emanating from the tissue which red component has been emitted by the light-emitting diode 16.

The collector of phototransistor 18 is connected to the positive terminal 30 of the power supply via a single resistor 29 with the same resistance as either resistors 27 or 28. While phototransistor 17 receives infrared radiation only, phototransistor 18 receives both the infrared radiation and the red light.

The electrical connection 40 between the series of resistors 27, 28 and the collector of phototransistor 17 is connected with the base of control transistor 25 via an RC circuit comprised of resistor 31 and capacitor 32 and also with an input terminal 33 of a comparator 34. The other input terminal 35 of the comparator 34 is connected with an electrical connection 45 between resistor 29 and the collector of phototransistor 18 via an RC circuit comprised of resistor 36 and capacitor 37. Both RC circuits are dimensioned so as to act as filters to suppress fluctuations of the photocurrents flowing through the phototransistors 17 and 18 with frequencies higher than 0.5 Hz and hence also the modulation of the photocurrents by the pulse rate of the blood.

By means of this comparator 34, the averaged DC component of the photocurrent flowing through phototransistor 18 and modulated by the pulse rate assumes twice the value of the DC component of the photocurrent flowing through the phototransistor 17 which is likewise modulated by the pulse rate.

An electrical connection 46 fixed between resistors 27 and 28 is connected with one input terminal 47 of a subtracting circuit 41 via a capacitor 38, and the electrical connection 45 between resistor 29 and phototransistor 18 via a capacitor 39 with the other input terminal 48 of the subtracting circuit 41. The subtracting circuit 41 has one output terminal 43 which serves as one final output of the whole circuit shown in FIG. 3. There is one direct output terminal 43 in the subtracting circuit 41 while another output terminal 44 of this whole circuit is directly connected to the capacitor 38. Thus, the subtracting circuit 41 consists of the operational amplifier 42 and a network of resistors.

The circuit shown in FIG. 3 operates in the following manner:

The light-emitting diodes 15 and 16 emit red and infrared radiation into the tissue of the finger or toe on which the cap 1 has been placed. After passing through the tissue, these flows of radiation impinge as a mixture of radiation, on the one hand, on phototransistor 17 via the green filter 20 and, on the other hand, directly on phototransistor 18. Accordingly, phototransistor 17 is only stimulated by the residual infrared radiation contained in the mixture of radiation, whereas phototransistor 18 is stimulated by both the residual infrared radiation and the residual red light. Since both phototransistors 17 and 18 are identical and are operated at the same point of their characteristics, the averaged direct current resulting from the infrared radiation in both transistors 17 and 18 can be assumed to be equal to the averaged direct current resulting from the red light and flowing additionally through phototransistor 18. For the electronic evaluation of the currents, it is, therefore, favorable for these direct currents, which are averaged with respect to time, i.e., the components of the photocurrents which do not exhibit modulation by the pulse rate and which are caused, on the one hand, by the red light and, on the other hand, by the infrared radiation, to be equal during evaluation since the two modulations caused by the two wavelength ranges—red and infrared—are then directly comparable. In order to avoid influences on the modulations by the DC component of the photocurrents, the control transistor 26 for the light-emitting diode 16 emitting red light is, therefore, controlled by the comparator 34 as soon as the voltages at input terminals 33 and 35 of comparator 34 show a difference.

By means of this arrangement, the averaged DC component of the photocurrent flowing through phototransistor 18 which indicates the red and the infrared radiation is always precisely twice as large as the averaged DC component of the photocurrent flowing through phototransistor 17 which indicates the infrared radiation only.

The components of the photocurrents flowing through the two phototransistors 17 and 18 and modulated by the heartbeat with a frequency of more than 0.5 Hz are tapped at the identical resistors 27 and 29, respectively, and subtracted from each other in the subtracting circuit 41. Accordingly, a signal resulting from the infrared radiation is available at the output terminal 44 and a signal resulting from the red light is available at the output terminal 43. As, for example, described in the chapter "NON-INVASIVE SPECTROPHOTOMETRIC ESTIMATION OF ARTERIAL OXYGEN SATURATION" of the book "Non-Invasive Measurements" by I. Yoshiya and Y. Shimada, published by Academic Press Inc. in 1983, the saturation of the blood with oxygen can be computed from the values represented by these currents.

In order to ensure excitation of each of the two identical phototransistors 17 and 18 by an equal intensity of the infrared radiation contained in the mixture of light, phototransistor 18 for the red light and the infrared radiation may be covered by a red filter 20' allowing the infrared radiation to pass to the same extent as the green filter 20 and, of course, reducing the flow of red light at the most to approximately the same extent.

All of the features mentioned in the above description and also those apparent from the drawings only are to be construed as further developments within the scope of the invention, even if they are not specially emphasized and, in particular, are not recited in the claims appended hereto.

What is claimed is:

1. A method for the determination of the saturation of the blood of a living organism with oxygen, comprising the steps of:
   simultaneously beaming into living tissue two separate beams of radiation in a first and in a second wavelength range, respectively, in which the absorption coefficients of oxyhemoglobin ($HBO_2$), on the one hand, and reduced hemoglobin (Hb), on the other hand, show different ratios for producing a mixed residual radiation emanating from the irradiated living tissue;

receiving from the mixed residual radiation
  (i) residual radiation in the first wavelength range via a first optoelectronic receiver element, and
  (ii) residual radiation in a larger measuring range, encompassing the first and the second wavelength ranges, via a second optoelectronic receiver element;

measuring the intensities of the two received residual radiations by means of photocurrents caused by said residual radiations in the respective receiver elements; and subtracting a measured intensity of the residual radiation in the first wavelength range from a measured intensity of the residual radiation in the larger measuring range by an electronic circuit means for determining the intensity of the residual radiation of the second wavelength range.

2. The method as defined in claim 1, comprising the further steps of:
  selecting initially a first beam having a first wavelength range in which absorption coefficients of oxyhemoglobin and reduced hemoglobin differ to as small an extent as possible; and
  selecting initially a second beam having a second wavelength range in which a difference between the absorption coefficients is as large as possible.

3. The method as defined in claim 1, comprising the further steps of:
  using as the first wavelength range an infrared radiation; and
  using as the second wavelength range a red light wave band.

4. The method as defined in claim 1, comprising the further steps of:
  using as the first and second optoelectronic receiver elements two identical receiver elements; and
  arranging in front of the first optoelectronic receiver element a filter means for blocking the residual radiation of the second wavelength range.

5. The method as defined in claim 1, comprising the further steps of:
  using RC-circuit means for smoothing the photocurrents of the first and the second receiver elements; and
  controlling the smoothed photocurrent of the second receiver element by an electronic comparator means for obtaining a value of the smoothed photocurrent of the second receiver element which value is twice as large as the value of the smoothed photocurrent of the first receiver element.

6. An electronic circuit for determining the saturation of the blood of a living organism with oxygen by using radiation in a first and in a second wavelength range, in which ranges the absorption coefficients of oxyhemoglobin ($HBO_2$), on the one hand, and reduced hemoglobin (Hb), on the other hand, show different ratios, comprising:
  first and second optoelectronic transmitting means for simultaneously beaming two separate beams of radiation in the first and the second wavelength ranges, respectively, into living tissue supplied with blood to be examined;
  first and second electronic control means for powering the first and second transmitting means, respectively;
  first and second identical optoelectronic receiver elements, each having a front means for receiving residual radiation emanating from the irradiated living tissue and for measuring radiation from first and second photocurrents conducted by the first and second receiver elements, respectively, depending on the received residual radiation;
  two first resistors being connected in series by a resistor connecting line and having substantially equal resistances, one end of the series being connected to the first receiver element by a first connecting line and the other end of the series being connected to a terminal of a supply means for powering the first receiver element and for conducting the first photocurrent;
  a second resistor, having substantially the same resistance as each of the two first resistors, one end of the second resistor being connected to the second receiver element by a second connecting line and the other end of the second resistor being connected to a terminal of a supply means for powering the second receiver element and for conducting the second photocurrent;
  a filter having a transparency for the residual radiation of the first wavelength range and blocking the residual radiation of the second wavelength range, said filter being arranged to cover the front means of the first receiver element;
  a comparator having a first and a second input terminal and one output terminal;
  a first RC circuit means for linking the first connecting line to the first input terminal of the comparator and to the first electronic control means in order to control the powering of the first transmitting means;
  a second RC circuit means for linking the second connecting line to the second input terminal of the comparator, said output terminal of the comparator being connected to the second electronic control means in order to control the powering of the second transmitting means, such that the second electronic control means for the radiation within the second wavelength range is controlled by the comparator when inputs at the first and second input terminals of the comparator show a difference, thus obtaining a DC component of the second photocurrent which is twice as large as a DC component of the first photocurrent;
  an electronic subtraction circuit having a first and a second input terminal and one output terminal;
  a first capacitor having a first and a second terminal, said first terminal of the first capacitor being connected to the first input terminal of the subtraction circuit and said second terminal of the first capacitor being connected to the resistor connecting line conducting the first photocurrent;
  a second capacitor having two terminals, one of which is connected to the second input terminal of the subtraction circuit and the other of which is connected to the second connecting line conducting the second photocurrent; and
  a first and a second final output terminal, said first final output terminal being connected to the first input terminal of the subtraction circuit and said second final terminal being said output terminal of the subtraction circuit;
  whereby a signal resulting from the residual radiation within the first wavelength range emanates from the first final output terminal and a signal resulting from the residual radiation within the second wavelength range emanates from the second final output terminal.

7. The electronic circuit as defined in claim 6, further comprising:
a second filter covering the front means of the second receiver element and having a transparency for the residual radiation of both first and said second wavelength ranges, said transparency of the second filter for the residual radiation of the first wavelength range being the same as the transparency of the first filter for the residual radiation of the first wavelength range.

* * * * *